United States Patent [19]

Sandrock et al.

[11] 4,297,286
[45] Oct. 27, 1981

[54] PROCESS FOR SELECTIVELY PRODUCING ISOSORBIDE-5-NITRATE

[75] Inventors: Klaus Sandrock, Langenfeld; Günter Cordes, Leichlingen, both of Fed. Rep. of Germany

[73] Assignee: Sanol Schwarz-Monhein GmbH, Monhein, Fed. Rep. of Germany

[21] Appl. No.: 114,906

[22] Filed: Jan. 24, 1980

[30] Foreign Application Priority Data

Feb. 2, 1979 [DE] Fed. Rep. of Germany ....... 2903927

[51] Int. Cl.$^3$ ............................................. C07D 307/00
[52] U.S. Cl. ............................... 260/347.8; 260/347.4; 424/285
[58] Field of Search ................... 260/346.11, 466, 467, 260/347.4, 347.8; 424/285, 298

[56] References Cited

U.S. PATENT DOCUMENTS 3,886,186  5/1975  Dvonch et al. ................... 260/347.8
4,065,488  12/1977  Chou et al. ......................... 260/467
4,156,736  5/1979  Cordes et al. ....................... 425/285

*Primary Examiner*—Edward A. Miller
*Attorney, Agent, or Firm*—Dennis P. Clarke

[57] ABSTRACT

The present invention is related to a new process for selectively preparing isosorbide-5-nitrate (1.4-3.6-dianhydrosorbitol-5-nitrate) by subjecting isomannide (1.4-3.6-dianhydromannitol) in an organic solvent or an aqueous-organic reaction medium to reaction with the equivalent amount of an acid halogenide or the anhydride of a benzene or naphthalene sulfonic acid possibly substituted by lower alkyl, lower alkoxy and/or halogen, of a perfluoro - lower alkane-sulfonic acid, of a lower alkanesulfonic acid or of a perfluoro - lower - alkanoic acid or with the equivalent amount of an acid halogenide of a carbamic acid or of sulphurous acid; subjecting the resulting isomannide-2-ester in the presence of a solvent and possibly with heating, to reaction with an alkali metal salt or an ammonium salt of a benzoic acid possibly substituted by lower alkyl, lower alkoxy and/or halogen or of a lower alkanoic acid; converting the hydroxy group in the 5-position of the resulting isosorbide-2-ester into the nitric acid ester group in manners known per se by reaction with nitric acid; and subjecting the resulting isosorbide-2-ester-5-nitrate to selective hydrolysis and/or reesterification in an organic or aqueous-organic solvent with an alkali metal hydroxide in manners known per se.

6 Claims, No Drawings

PROCESS FOR SELECTIVELY PRODUCING ISOSORBIDE-5-NITRATE

The present invention is related to a new process for producing 1.4–3.6-dianhydrosorbitol-5-nitrate having the formula

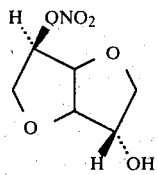

and the international generic name isosorbide-5-nitrate.

Isosorbide-2.5-dinitrate (ISD) is a product known since long and used since many years in the treatment of coronary heart diseases such as angina pectoris. Many pharmaceutical preparations of this compounds are trade products. This compound upon oral administration is subject to a strong first-pass-effect in the liver, i.e. metabolites are produced such as isosorbide-2-mononitrate (2-ISM), isosorbide-5-mononitrate (5-ISM), isosorbide, sorbitol as well as corresponding conjugates (Sisenwine and Ruelius, J. Pharmacol. Exper. Therap., vol. 176 (1970) p. 296; Chasseaud et al., Europ. J. Clin. Pharmcol., vol. 8 (1975) p. 157; Chasseaud and Down, J. Pharm. Sci., vol. 63 (1974) p. 1147). It has been shown in these investigations that Isosorbide-2-nitrate and isosorbide-5-nitrate produce the same effects as isosorbide-2.5-dinitrate and that therefor the activity of the administered isosorbide-2.5-dinitrate is partially caused by the mononitrates produced by this metabolism (R. L. Wendt, J. Pharmacol. Exper. Therap., vol. 180 (1971) p. 732; Michel, Herz-Kreislauf Nr. 8 (1976) p. 444; Stauch et al., Verh. Dtsch. Ges. Kreislaufforschg., vol. 41 (1975) p. 182).

The investigations further showed that the administration of the moninitrates, in particular of the isosorbide-5-nitrate may be advantageous over the administration of isosorbide-2.5-dinitrate if for instance the first-pass-effect with the mononitrate is less strong and the individual variations in the degree of conversion by metabolism are accordingly less. However, up to now, the complicated and very expensive methods for producing this compound known up to now was a bar to the direct application thereof.

According to I. G. Csizmadia and D. L. Hayward, Photochem. Photobiol., vol. 4 (1965) p. 657, isosorbide-5-nitrate is produced by direct nitration of isosorbide (1.4–3.6-dianhydrosorbitol). A mixture of nitrates is obtained thereby containing isosorbide-5-nitrate only in minor amounts. This compound is separated from this mixture by adsorption chromatographic methods. The yields in isosorbide-5-nitrate are very low and the isolation procedures are so time consuming and expensive that this manner of producing isosorbide-5-nitrate never became of practical importance.

In a second method isosorbide-2.5-dinitrate is produced at first from isosorbide by known methods. The resulting isosorbide-2.5-dinitrate thereafter is partially saponified again resulting in a mixture of isosorbide-2.5-dinitrate, isosorbide-2-nitrate, isosorbide-5-nitrate and isosorbide which have to be separated again by the above time comsuming and expensive methods and have to be isolated (Anteunis et al., Org. Magnetic Resonance, vol. 3 (1971) p. 363; D. L. Hayward et al, Can. J. Chem., vol. 45 (1967) p. 2191).

Finally, German published patent application No. P 27 51 934 and the corresponding U.S. Pat. No. 4,065,488 describe a process wherein isosorbide in a first step is esterified by reaction with a lower alkanoic anhydride, chloride or bromide, in particular acetic acid anhydride, to yield a mixture of isosorbide, isosorbide-2-acrylate, isosorbide-5-acylate and isosorbide-2.5-diacylate. In a second step, isosorbide is extracted from this mixture in order to avoid formation of isosorbide-2.5-dinitrate in the following nitration reaction which is dangerous as explosive. In a third step, the mixture of isosorbide-2-acylate, isosorbide-5-acylate and isosorbide-2.5-diacylate is subjected to nitration with nitric acid and the resulting mixture of isosorbide-2-acylate-5-nitrate, isosorbide-5-acylate-2-nitrate and isosorbide-2.5-diacylate is subjected to partial saponification resulting in a mixture of isosorbide-2-nitrate, isosorbide-5-nitrate and isosorbide. Isosorbide-5-nitrate finally is separated from this mixture by recrystallization from appropriate solvents. Thus, this process also is characterized by a multitude of reaction steps and has the further disadvantage that isosorbide contained in the mixture obtained in the first reaction step, has to be extracted in order to avoid the formation of the explosive isosorbide-2.5-dinitrate in the subsequent nitration reaction.

It is common to all known processes that isosorbide-5-nitrate cannot be produced selectively but that mixtures are always obtained which have to be split up by suitable separation procedures such as adsorption chromatography or recrystallization. Such separation procedures, in particular chromatographic methods, however are time and cost consuming. They allow only rather low yields in the desired final product. The production of isosorbide-5-nitrate by such processes therefor is rather expensive.

The present invention is related to a process for selectively producing isosorbide-5-nitrate. It is characterized in that (a) isomannide (1.4–3.6-dianhydromannitol) is subjected to reaction with heating with the equivalent amount of an acid halide (preferably an acid chloride or bromide, most preferably an acid chloride) of an aromatic sulfonic acid of the general formula I

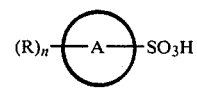

wherein A is a benzene or a naphthalene ring (preferably a benzene ring), R is a lower alkyl with 1 to 4 carbon atoms (preferably methyl), a lower alkoxy with 1 to 4 carbon atoms (preferably methoxy) or a halogen (preferably chlorine or bromine) and n is a numeral from 0 to 3 (preferably 0 or (1), or of a perfluoro-lower alkane sulfonic acid with 1 to 4 carbon atoms (preferably with 1 or 2 carbon atoms, in particular trifluoromethylsulfonic acid), or of a lower alkane sufonic acid with 1 to 4 carbon atoms (preferably with 1 or 2 carbon atoms, in particular methanesulfonic acid) or of a perfluoro-lower alkanoic acid with 1 to 4 carbon atoms in the alkane group (preferably with 1 or 2 carbon atoms in the alkane group, in particular trifluoroacetic acid) or of a carbamic acid or of sulphurous acid, in the presence of an acid binding agent, or is subjected to reaction with heating with an equivalent amount of the anhydride of the above aromatic sulfonic acid of the general formula I, perfluoror-lower alkane sulfonic acid, alkane sulfonic acid or perfluoro acid, (b) the resulting isomannide-2-ester in the presence of a solvent and possibly with heating, is subjected to reaction with an alkali metal salt or ammonium salt of a benzoic acid having the general formula II

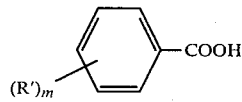

wherein R' is a lower alkyl group with 1 to 4 carbon atoms (preferably methyl), a lower alkoxy group with 1 to 4 carbon atoms (preferably methoxy) or a halogen (preferably fluorine, chlorine or bromine, in particular chlorine or bromine) and m is a numeral between 0 and 3 (preferably 0 or 1), or of a lower alkanoic acid with 1 to 4 carbon atoms in the alkane group (preferably 1 or 2 carbon atoms in the alkane group, in particular acetic acid) or of formic acid, (c) the free hydroxy group in the 5-position of the resulting isosorbide-2-ester is nitrated, i.e. is converted into the nitric acid ester group —$ONO_2$, with nitric acid in manners known per se, and (d) the resulting isosorbide-2-ester-5-nitrate is selectively hydrolysed in manners known per se in an organic or aqueous-organic solvent with an alkali metal hydroxide and/or is reesterified, thus splitting off the ester group in the isosorbide-2-ester-5-nitrate with the partial or complete formation of another ester of the benzoic acid split off from the isosorbide-5-nitrate molecule (for instance, isosorbide-2-benzoate-5-nitrate is converted into another benzoic acid ester besides isosorbide-5-nitrate).

It is preferred to subject isomannide in the first reaction step to reaction with the acid chloride, bromide or anhydride of p-toluene sulfonic acid, trifluoromethane sulfonic acid, methane sulfonic acid or trifluoroacetic acid.

According to a preferred embodiment of the process of the present invention, isomannide in the first step is reacted in such an organic solvent or aqueous-organic reaction medium in such an amount that the resulting isomannide-2-ester is precipitated substantially completely. This increases the yield to a surprising extent. When using the most preferred p-toluene sulfonic acid, the aqueous-organic reaction medium is an immiscible organic-aqueous medium the organic phase whereof being a mixture of carbontetrachloride $CCl_4$ and methylenedichloride $CH_2Cl_2$ in a volume proportion of 9:1.

Ammonium salts used in the second step of the present process also comprise quaternary ammonium salts. Preferred ammonium salts are those of ammonia $NH_3$ and of the amines $N(R_2)_3$ wherein $R_2$ is hydrogen or $C_1$ to 4-lower alkyl (preferably $C_1$ to 2-lower alkyl) and at least one of $R_2$ is such a lower alkyl group, and tetra-($C_1$ to 4-lower alkyl) ammonium salts (preferably the tetra-n-butyl-ammonium salts).

According to another preferred embodiment of the present process, the isomannide-2-ester obtained in the first reaction step is subjected to reaction with an alkali metal salt of benzoic acid, preferably with the potassium salt of benoic acid, or with tetrabutylammonium acetate or formate. Suitable solvents in the second step of the process of the present invention are purely aqueous, aqueous-organic or purely organic solvents, in particular acetone, dimethylformamide acetonitrile or glycol or diglycol ethers (so-called glyme solvents) or mixtures of several such solvents. The isomannide-2-ester most preferably is reacted with sodium benzoate in dimethylformamide.

The nitration of the free hydroxy group in the 5-position of the isosorbide-2-ester is for instance carried out by subjecting the ester to reaction with concentrated nitric acid in a mixture of acetic acid and acetic anhydride. Such a reaction is known for instance from Hayward et al., Can. J. Chem., vol. 45 (1967) p. 2191. The splitting off of the 2-ester group is accomplished by hydrolysis in an aqueous-organic solvent with an alkali metal hydroxide or by alcoholysis in an organic solvent comprising an alcohol with an alkali metal hydroxide as described in detail in published German patent application No. P 27 51 934 in connection with other polyhydroxy compounds, or in ethyl alcohol in the presence of sodium or potassium ethylate. The following examples serve to further illustrate the present invention without however limiting the same thereto.

EXAMPLE 1

(a) Isomannide-2-p-toluenesulfonic acid ester 730.7 g of isomannide and 308.6 g of potassium hydroxide are dissolved in 4.6 l of water. A solution of 1070.0 g of p-toluenesulfonic acid chloride in 3.6 l of carbontetrachloride and 0.4 l of methylene dichloride is added thereto at +5° C. The mixture is vividly stirred at +5° C. for 6 hours. Isomannide-2-p-toluenesulfonic acid ester is precipitated continuously. Thereafter, the reaction product is filtered off with suction and washed with a mixture of 0.4 l of carbontetrachloride and 0.1 l of methylene dichloride and dried in a water pump vacuum. 1073.0 g of isomannide-2-p-toluenesulfonic acid ester are obtained melting at 105.5° C.

Yield: 71.5% of the theoretical, calculated to the amount of isomannide started from.

This product may also be obtained in that the isomannide is dissolved in 3.35 l of water, the solution of p-toluenesulfonylchloride is added thereto and the potassium hydroxide dissolved in 1.25 l of water is then added thereto dropwise with vivid stirring at +5° C. Stirring is continued at +5° C. for 3 hours and the resulting reaction mixture is further worked up as above described. Fp.: 105.5° C.

Yield: 74.9% of the theoretical, calculated to the amount of isomannide started from.

(b) Isosorbide-2-benzoate 1073.0 g of isomannide-2-p-toluenesulfonic acid ester and 574.7 g of potassium benzoate in 2.8 l of dimethylformaide are refluxed with stirring for 2 to 4 hours. The resulting reaction mixture is cooled to 100° to 110° C. and poured upon 10 l of ice-water. The mixture is extracted three times with each 2 l methylene dichloride. The combined extracts are washed twice with each 1.5 l of a saturated aqueous solution of sodium hydrogencarbonate $NaHCO_3$ and once with 1.5 l of 1 N hydrochloric acid. The resulting methylene dichloride solution is heated to boiling with 88 g of activated charcoal, filtered and evaporated. There are obtained about 850 g of oily yellow-brownish isosorbide-2-benzoate.

(c) Isosorbide-2-benzoate-5-nitrate.

A mixture of 432.9 g of acetic anhydride and 254.6 g of 100% acetic acid is cooled to about −5° C. and 244.4 g of 100% nitric acid are added thereto dropwise such that the temperature of the mixture is maintained between −5° C. and 0° C.

850 g of the oily isosorbide-2-benzoate are dissolved in 1400 cc. of methylene dichloride and the solution is cooled to about 15° C. The above nitric acid mixture is added thereto dropwise such that the temperature of the resulting reaction mixture does not exceed 25° C. The mixture is allowed to stand at room temperature over night and thereafter is poured with stirring upon 2.5 l of ice-water. The organic phase of the resulting mixture is separated and the aqueous phase is extracted once with 1000 cc. of methylene dichloride. The combined methylene dichloride extracts are washed once with 1 l of water and twice with each 1 l of a saturated aqueous sodium hydrogencarbonate solution. The resulting solution is evaporated until an oily residue is obtained.

Yield: 955.8 g of isosorbide-2-benzoate-5-nitrate.

(d) Isosorbide-5-nitrate 955.8 g of isosorbide-2-benzoate-5-nitrate are dissolved in 4500 cc. of ethanol with stirring at 50° C. A solution of 45.5 g of potassium hydroxide in 500 cc. of ethanol is added thereto and the mixture is stirred for 15 to 30 minutes at a temperature of 50° C. After cooling to room temperature, 25% hydrochloric acid is added with stirring until a pH of 6.5 to 7.5 is reached. The reaction mixture is evaporated to dryness and the residue is dissolved with heating in 1 l of a saturated aqueous sodium hydrogencarbonate solution. This solution is extracted once with 3 l of methylene dichloride and four times with each 1 l of the same solvent. The combined methylene dichloride extracts are evaporated to dryness. The oily residue is mixed with heating and vivid stirring with 1.5 l of hexane or carbontetrachloride in order to remove benzoic acid ethyl ester. The resulting mixture then is cooled to room temperature with continued stirring. The precipitated product is filtered off with suction, washed with hexane or carbontetrachloride and dried. The resulting crude isosorbide-5-nitrate (about 532 g) is dissolved in 1000 cc. of boiling chloroform and 1000 cc. of carbontetrachloride is added thereto slowly at boiling temperature. From the resulting solution at room temperature 475.1 g of isosorbide-5-nitrate are separated by crystillization. The product crystallizes as colorless needles. F.p.: 91.0° C.

Yield: 69.5% of the theoretical, calculated to isomannide-2-p-toluenesulfonic acid ester or 49.7% of the theoretical, calculated to isomannide.

EXAMPLE 2

Isomannide-2-p-toluenesulfonic acid ester 146 g of isomannide are dissolved in 174 g of pyridine and 900 cc. of methylene dichloride. After cooling to +5° C., 208 g of p-toluenesulfonylchloride dissolved in 900 cc. of methylene dichloride are added thereto dropwise within 4 hours and the resulting reaction mixture is allowed to stand over night. The solution thereafter is washed with 430 cc. of 25% hydrochloric acid and 430 cc. of a saturated aqueous sodium hydrogencarbonate solution and dried over anhydrous sodium sulphate. After evaporation, the oily residue is dissolved in boiling methanol. Upon cooling, isomannide-2.5-di-p-toluenesulfonic acid ester precipitates. This product is filtered off with suction and the volume of the filtrate is doubled by the addition of water. The resulting precipitated product is filtered off. 113 g of isomannide-2-p-toluenesulfonic acid ester melting at 105.8° C. are obtained which is further reacted as described in Examples 1b to 1d to isosorbide-5-nitrate.

Yield: 37.7% of the theoretical, calculated to isomannide.

EXAMPLE 3

Isosorbide-5-nitrate 690.9 g of the oily isosorbide-2-benzoate-5-nitrate prepared as described in Example 1c, are dissolved in 2.8 l of ethanol at 50° C. with stirring. A solution of 187.2 g of sodium hydroxide in 1 l of water is added thereto and the mixture is stirred for 45 minutes at a temperature of 50° C. After cooling to room temperature, about 250 cc. of 37% hydrochloric acid is added thereto to give a pH of 6. The volume of the reaction mixture is decreased to 1 l and the resulting solution is acidified by the addition of 37% hydrochloric acid in order to precipitate benzoic acid. The precipitated benzoic acid is filtered off with suction, 2 l of water are added to the filtrate with vivid stirring and the mixture is again filtered with suction. The two aqueous filtrates are combined and an aqueous 30% sodium hydroxide solution is added until a pH of 6 is reached. The volume of the resulting mixture is decreased to 800 cc. Thereafter, the mixture is extracted four times with each 1 l of methylene dichloride.

The combined methylene dichloride extracts are washed once with 200 cc. of a saturated aqueous sodium hydrogencarbonate solution. The aqueous phase is washed once with 500 cc. of methylene dichloride. The combined methylene dichloride extracts are evaporated to dryness and the residue (313.3 g) is dissolved in boiling chloroform. 600 cc. of carbontetrachloride are slowly added thereto at boiling temperature and the resulting mixture is cooled to room temperature. 277.6 g of isosorbide-5-nitrate are obtained as colorless needles. F.P.: 90.0° C.

We claim:

1. A process for preparing isosorbide-5-nitrate comprising
   (a) reacting isomannide in an organic solvent or in an aqueous-organic reaction medium with an equivalent amount of a compound selected from the group consisting of:
   (1) the acid halogenides of an aromatic sulfonic acid of the general formula I

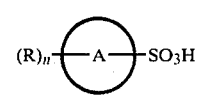

I wherein A is a benzene or a naphthalene ring, R is a lower alkyl group with 1 to 4 carbon atoms, a lower alkoxy group with 1 to 4 carbon atoms or a halogen, and n is a numeral from 0 to 3,
   (2) a perfluoroalkanesulfonic acid with 1 to 4 carbon atoms or anhydride thereof,
   (3) an alkanesulfonic acid with 1 to 4 carbon atoms or anhydride thereof, (4) a perfluoroalkanoic acid with 1 to 4 carbon atoms or anhydride thereof,
(5) a carbamic acid, and
(6) sulphurous acid;
(b) reacting the resulting isomannide-2-ester in the presence of a solvent with a compound selected from the group consisting of:
(1) the alkali metal and ammonium salts of a benzoic acid of the general formula II

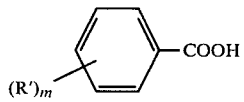

wherein R' is a lower alkyl group with 1 to 4 carbon atoms, a lower alkoxy group with 1 to 4 carbon atoms or a halogen, and m is a numeral from 0 to 3, and
(2) a lower alkanoic acid with 1 to 4 carbon atoms in the alkane group, at a temperature sufficient to produce an isosorbide-2-ester,
(c) converting the hydroxy group in the 5-position of the resulting isosorbide-2-ester into the nitrate group by subjecting the ester to reaction with nitric acid, and
(d) splitting off the 2-ester group from the resulting isosorbide-2-ester-5-nitrate to yield the isosorbide-5-nitrate by hydrolysis in an aqueous organic solvent with an alkali metal hydroxide or by alcoholysis in an organic solvent comprising an alcohol with an alkali metal hydroxide.

2. The process of claim 1 wherein isommanide is subjected to reaction with a compound selected from the group consisting of the acid chlorides, bromides or anhydrides of p-toluene-sulfonic acid, trifluoromethane-sulfonic acid, methanesulfonic acid and trifluoroacetic acid.

3. The process of claim 1 or 2 wherein isomannide in the first reaction step (a) is reacted in an organic solvent or aqueous-organic reaction medium in an amount such that the resulting isomannide-2-ester is precipitated substantially completely therefrom.

4. The process of claim 3 wherein isomannide in the first reaction step (a) is subjected to reaction with a compound selected from the group consisting of the acid chloride and anhydride of p-toluene-sulfonic acid in an immiscible organic-aqueous reaction medium the organic phase thereof consisting of a mixture of carbontetrachloride and methylene dichloride in a volumetric proportion of 9:1.

5. The process of claim 1 wherein the isomannide-2-ester resulting from the first reaction step (a) is reacted with a compound selected from the group consisting of the alkali metal salts of benzoic acid, tetrabutylammoniumacetate and tetrabutylammoniumformiate.

6. The process of claim 5 wherein the isomannide-2-ester is reacted with potassium benzoate in dimethylformamide.

* * * * *